United States Patent
Tanaka et al.

(10) Patent No.: US 6,572,589 B2
(45) Date of Patent: Jun. 3, 2003

(54) BARREL MOUNTING DEVICE IN CARTRIDGE-TYPE DENTAL INJECTION DEVICE

(75) Inventors: Fumio Tanaka, Tokyo (JP); Yukio Kawagishi, deceased, late of Tokyo (JP), by Kayoko Kawagishi, Masayuki Kawagishi, Youko Kawasaki, legal representatives (73) Assignee: Showa Yakuhin Kako Co., Ltd. (JP)

( * ) Notice: Subject to any disclaimer, the term of this patent is extended or adjusted under 35 U.S.C. 154(b) by 0 days.

(21) Appl. No.: 10/138,707

(22) Filed: Apr. 30, 2002

(65) Prior Publication Data

US 2002/0193750 A1 Dec. 19, 2002

Related U.S. Application Data (63) Continuation of application No. PCT/JP00/07695, filed on Nov. 1, 2000.

(30) Foreign Application Priority Data

| Nov. 5, 1999 | (JP) | .............................................. 11-315280 |
| Dec. 27, 1999 | (JP) | .............................................. 11-369949 |

(51) Int. Cl.[7] .............................................. A61M 5/00
(52) U.S. Cl. ...................................... 604/234; 604/232
(58) Field of Search ................................. 604/181, 182, 604/187, 188, 221, 223, 228, 229, 232, 234, 241, 240, 242, 131; 128/DIG. 1

(56) References Cited

U.S. PATENT DOCUMENTS

| 1,718,599 | A | * | 6/1929 | Smith .......................... 604/232 |
| 1,718,600 | A | * | 6/1929 | Smith .......................... 604/232 |
| 2,966,910 | A | * | 1/1961 | Camber ....................... 604/232 |
| 4,585,445 | A |   | 4/1986 | Hadtke |
| 5,350,367 | A |   | 9/1994 | Stiehl et al. |
| 5,480,388 | A | * | 1/1996 | Zadini et al. ................ 604/165 |
| 5,738,659 | A | * | 4/1998 | Neer et al. ................... 604/131 |
| 5,827,234 | A | * | 10/1998 | Loos et al. .................. 604/236 |
| 6,312,410 | B1 | * | 11/2001 | Yamamoto ................... 604/152 |

FOREIGN PATENT DOCUMENTS

JP        6-52838 U       7/1994

* cited by examiner

*Primary Examiner*—Sharon Kennedy
(74) *Attorney, Agent, or Firm*—Nixon Peabody LLP; Donald R. Studebaker

(57) ABSTRACT

A cartridge type dental injection device capable of easily and quickly mounting or removing a cartridge loaded barrel in or from a socket therein and capable of altering orientations of a viewing window in the barrel and of a cut surface of a needle as desired.

The cartridge type dental injection device comprises a barrel (9) adapted to be inserted in a socket (5) defined by a mounting member (5a) and having diametrically oppositee viewing windows (11) formed therein, the mounting member (5a) having a plurality of circumferentially spaced apart ball retaining holes (7), and a locking ball (8) placed in each of the holes, the barrel (9) being provided with an annular groove (12) adapted to receive a portion of each locking ball therein, and a locking ring (13) having an annular cam surface (14) and a relieving surface (15) positioned adjacent to each other and movable between a position where when the locking balls (8) are in alignment with the annular groove (12), the annular cam surface (14) pushes the locking balls (8) toward the annular groove (12) to bring portions of the locking balls into engagement with the annular groove and a position where the relieving surface (15) faces the locking balls (8) to release them from the annular groove (12).

6 Claims, 7 Drawing Sheets

BARREL MOUNTING DEVICE IN CARTRIDGE-TYPE DENTAL INJECTION DEVICE

This is a continuation of PCT/JP00/07695 filed Nov. 1, 2000.

FIELD OF THE INVENTION

This invention generally relates to cartridge-type dental injectors, and more particularly, to a mounting device for a barrel adapted to receive a cartridge therein.

BACKGROUND ART

In a manual type dental injection device, a cartridge receiving barrel is secured to a body of the injection device by fastening means such as a cramping screw. The barrel is also provided with diametrically opposite viewing windows formed therein and having a sufficient size to insert the cartridge into the barrel. In case of an electrically powered dental injection device, a cartridge receiving barrel is removably mounted in a socket defined by a mounting member which is connected to a support member for a plunger rod, the support member being secured to a nose portion of a housing of the injection device. The barrel is removed from the socket after completion of injection so that the cartridge can be inserted in the barrel, and the barrel is again mounted in the socket for injection. The barrel is provided with diametrically opposite viewing windows.

It is well known that the cartridge includes a rubber plug retained at the end of the cartridge by a metallic cap for sealing and adapted to be penetrated with an needle of a needle fitting when it is threadedly secured to the barrel at its forward end, and a plunger rubber fitted in a rear open end of the cartridge, and adapted to be pushed by the plunger rod, thereby ejecting the injection liquid contained in the cartridge, through the needle.

In the injection device of either type, the viewing windows play a important role in enabling a condition of the cartridge to be visibly ascertained, that is to say, enabling it to be determined how much injection liquid in the cartridge has been injected therefrom. The needle has at the tip end a cut surface to provide a sharp cutting edge thereto, and it is required that the gums be pierced with the sharp cutting edge with the cut surface facing the teeth of a patient.

As each dentist has a particular physique or posture for treatment to a patient, this results in an angle at which the dentist can best view the cartridge through the viewing window being changed. It is therefore required that a dentist alters an angular position of the viewing window in the barrel to one at which it is easy for the dentist to view the cartridge in the barrel through the viewing window, as well as the orientation of the cut surface defining the sharp cutting edge of the needle, against the teeth. In the case of manual type injector, the cramping screw is loosened relative to the injector body to enable the angular position of the barrel to be altered, but such manual operations for loosening and then tightening the cramping screw are troublesome and inefficient. In the case of the electrically powered dental injection device, it is impossible to alter the orientation of the viewing window so that it is oriented with the cut surface of the needle, because the barrel is installed in the socket at a fixed position. Since the barrel is arranged to enable it to be removed from the socket whenever it is to be loaded with the cartridge, there is a need for a simplified arrangement for installing the barrel in the socket.

SUMMARY OF THE INVENTION

It is an object of the invention to provide a cartridge type dental injection device capable of easily altering the orientations of the viewing window and of the cut surface of the needle as desired.

This object of the invention can be achieved by providing a device for mounting cartridge receiving barrel in a cartridge type dental injection device comprising a mounting member having a socket, a barrel adapted to be inserted in the socket and having diametrically opposite viewing windows formed therein, the mounting member having a plurality of circumferentially spaced apart ball retaining holes, and a locking ball placed in each of the holes, the barrel being provided with an annular groove adapted to receive a portion of each locking ball therein, and a locking ring having an annular cam surface and a relieving surface positioned adjacent to each other and movable between a position where when the locking balls are in alignment with the annular groove, the annular cam surface pushes the locking balls toward the annular groove to bring portions of the locking balls into engagement with the annular groove and a position where the relieving surface faces the locking balls to release them from the annular groove.

According to the invention, the movement of the locking ring from the position where the locking balls are released from the annular groove, may be in a direction toward or away from the housing of the injection device.

In the preferred embodiment of the invention, a coil spring may be provided for urging the locking ring to the position where the annular cam surface faces the locking balls.

Furthermore, there may be provided means for determining the position to which the barrel can be inserted in the socket. Such means may comprise a shoulder of the barrel, adapted to abut the forward end of the barrel.

The mounting member defining the socket may have a piece of rubber tightly fitted in an aperture drilled therein, the piece of rubber being in frictional engagement with a portion of the peripheral surface of the barrel to prevent it from unintentionally turning around it's axis relative to the socket.

As the locking ring is manually pushed against action of the coil spring to the position where the relieving surface is opposite to the locking balls in the ball retaining holes, they are movable radially outwardly toward the relieving surface so that the barrel can be removed from or inserted in the socket for charge or removal of a cartridge, and when ceasing the pushing of the locking ring, it is returned to its original position under action of the coil spring so that the annular cam surface will engage the locking balls to push radially inwardly them into the annular groove, thereby preventing the barrel from coming out of the socket. In this position, the barrel is rotatable around it's axis so as to be capable of altering the orientations of the viewing window and cut surface of the needle secured to the barrel as desired. The piece of rubber apples enough braking to the barrel by frictional engagement with the outer peripheral surface of the barrel, to prevent it from unintentionally turning, thereby, maintaining the desired orientations of the viewing window and cut surface of the needle during injection.

DETAILED DESCRIPTION OF THE PREFERRED EMBODIMENTS

Figure 1:
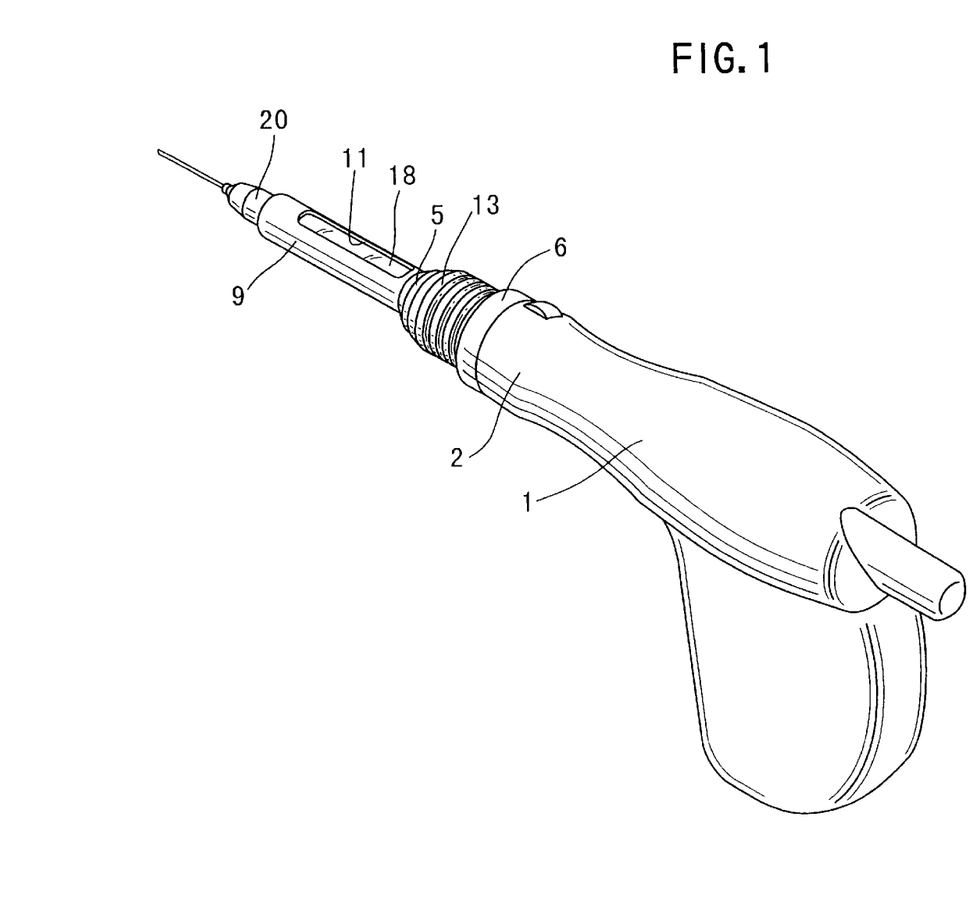
FIG. 1 is a perspective view of a cartridge type dental injection device according to a first embodiment of the present invention.
Figure 2:
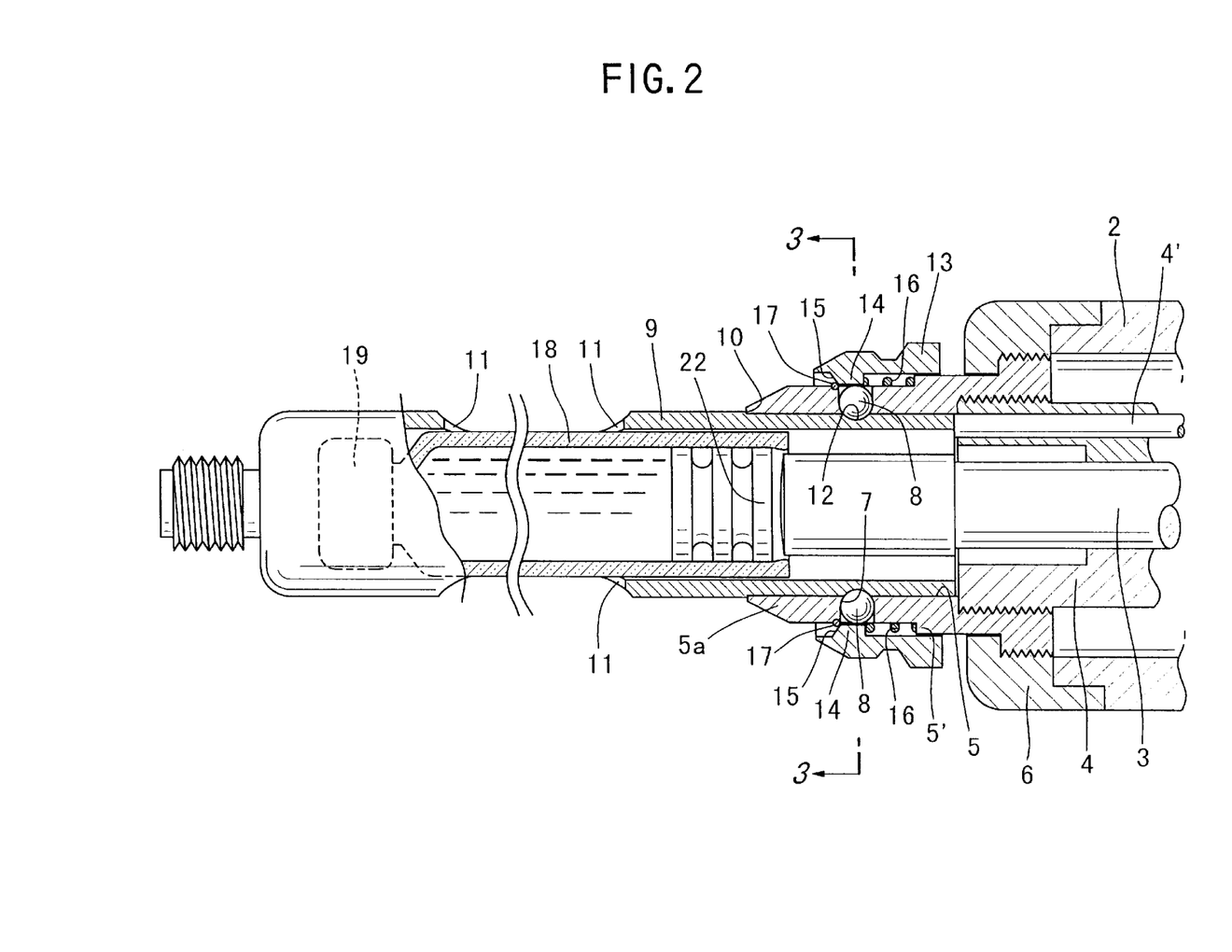
FIG. 2 is a fragmental view in section of the injection device, showing a mechanism for coupling a barrel to a socket of the device.
Figure 3:
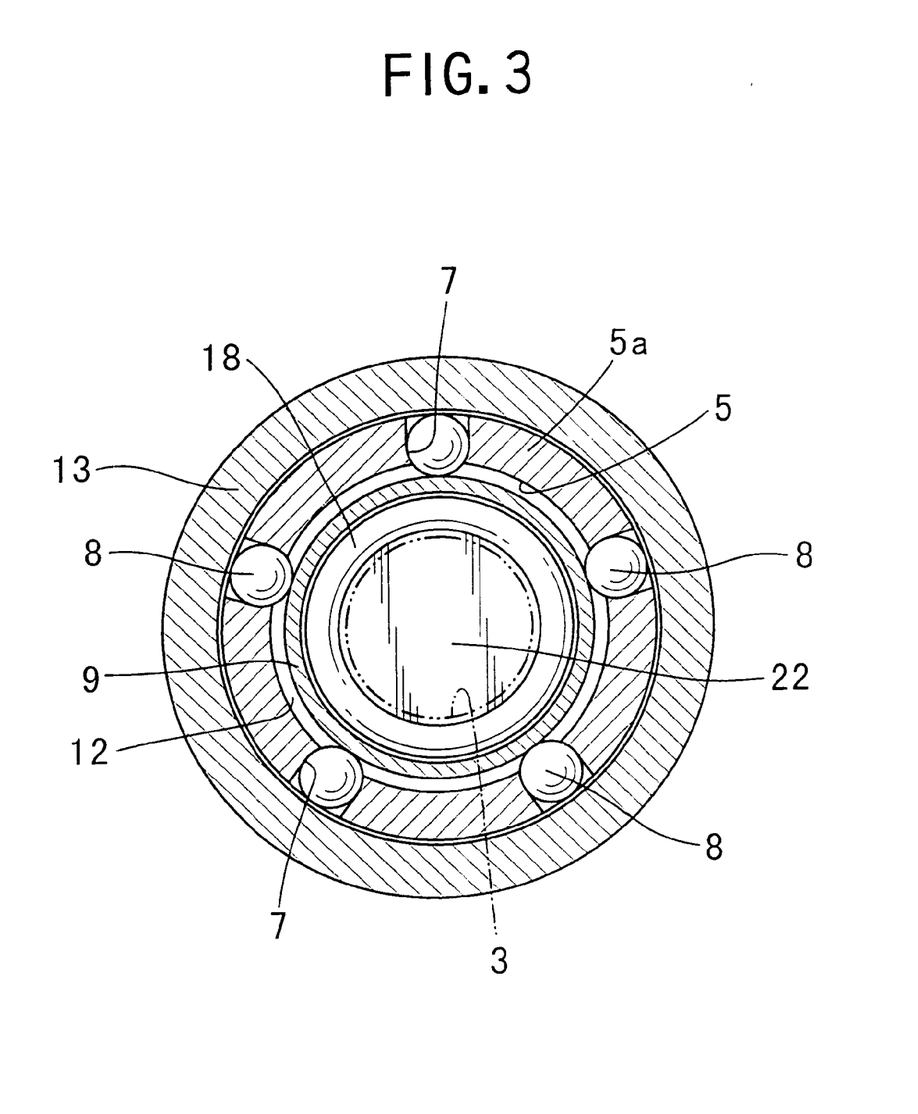
FIG. 3 is a cross-sectional view taken along line 3—3 of FIG. 2.

Referring to the accompanying drawings, a cartridge type electrically powered dental injection device is illustrated therein but it will be appreciated that the principle of the invention can be applied to a cartridge type manual dental injector. In FIGS. 1 and 2, the injection device of the invention includes a mounting member 5a threadedly connected to the forward end of a support member 4 secured to a nose portion 2 of a housing 1 of the injection device, in any suitable manner, for supporting a plunger rod 3 for sliding movement. The plunger rod 3 is adapted to be advanced at an extremely low speed by drive means. Reference numeral 6 indicates a retaining cap of the housing, threadedly secured to the mounting member 5a. As can be seen in FIGS. 2 and 3, the mounting member 5a includes a plurality of circumferentially spaced apart ball retaining holes 7 and locking steel balls 8 each placed in the hole 7. A barrel 9 is adapted be inserted into a socket 5 in the mounting member 5a and an extent of insertion of the barrel into the socket is restricted by a shoulder 10 on the barrel abutting against the forward end of the socket 5. The barrel 9 has diametrically opposite viewing windows formed therein and is provided with an annular groove 12 formed on the outer peripheral surface thereof and adapted to receive portions of the locking balls 8 therein. The mounting member 5a is provided on its outer periphery with a locking ring 13 which includes an annular cam surface 14 and a relieving surface 15 formed therein adjacent to each other. The locking ring 13 is movable between a position where when the locking balls 8 are in alignment with the annular groove 12, the annular cam surface 14 pushes the locking balls 8 toward the annular groove 12 to bring portions of the locking balls into engagement with the annular groove 12 and a position where the relieving surface 15 faces the locking balls 8 to release them from the annular groove 12. The movement of the locking ring 13 from the position where the locking balls are released from the annular groove 12, is in a direction toward the housing of the injection device. A coil spring 16 is disposed between a shoulder of the annular cam surface 14 of the annular locking ring 13 and a shoulder 5' formed on the outer periphery of the mounting member 5a to urge the locking ring 13 to the position where the annular cam surface 14 faces the locking balls 8, that is to say, in a direction away from the injection device. Reference numeral 17 indicates a stop ring fitted in a circumferential groove formed on the outer periphery of the mounting member 5a on the side of the relieving surface 15 of the locking ring 13 to serve to retain in place the locking ring 13 urged by the coil spring 16. In FIG. 2, reference numeral 4' indicates a control rod adapted to actuate the drive means of the injection device, the control rod 4' being pushed rearwardly with its rear end face when the barrel 9 is inserted into the socket.

Figure 4:
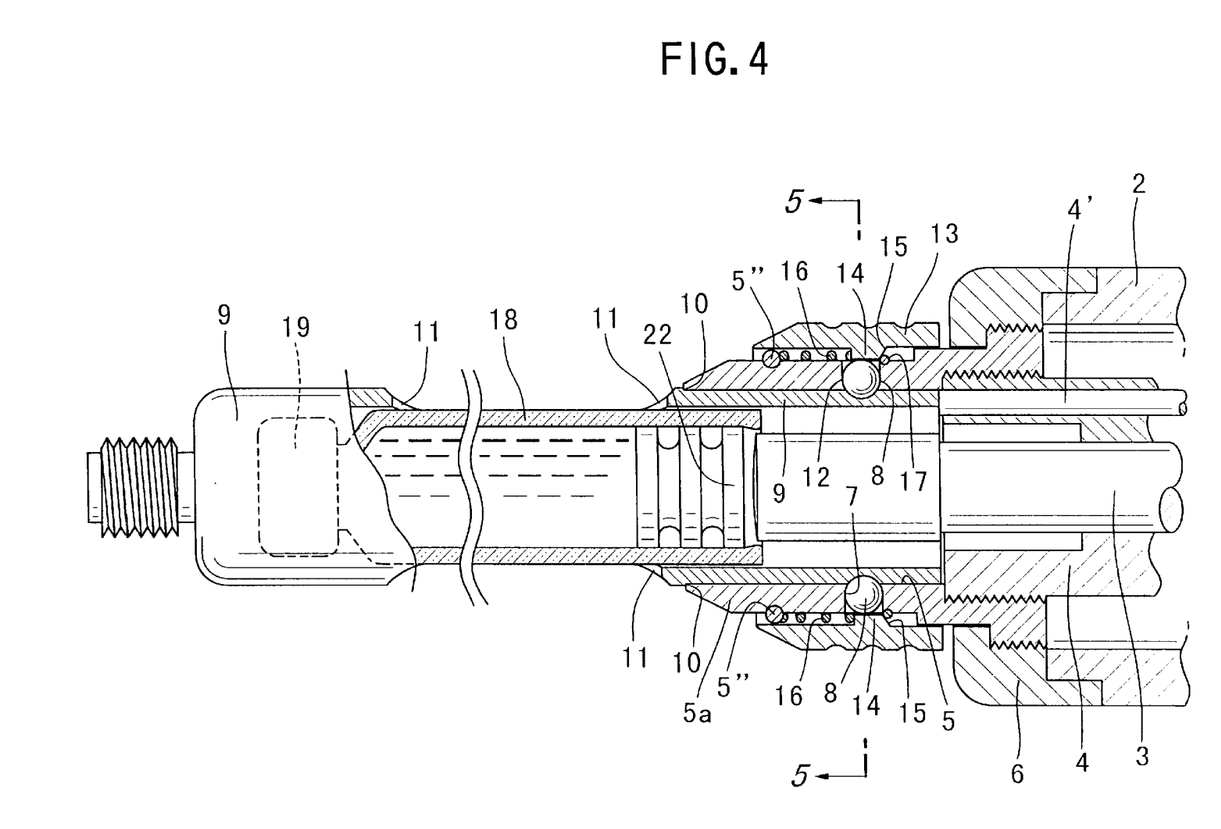
FIG. 4 is a view similar to FIG. 2, showing a cartridge type dental injection device according to a second embodiment of the present invention.
Figure 5:
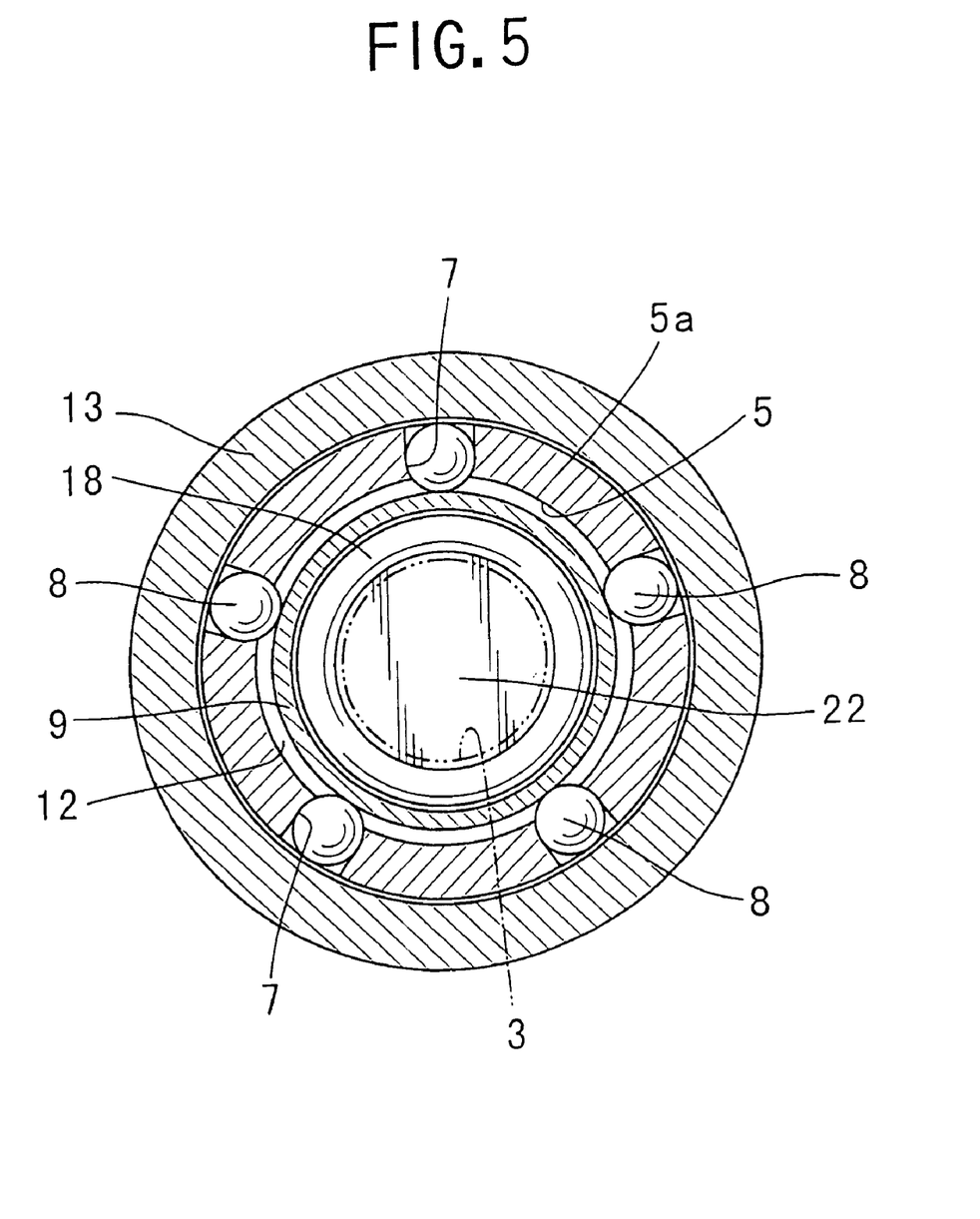
FIG. 5 is a cross-sectional view taken along line 5—5 of FIG. 4.

FIGS. 4 and 5 illustrate another embodiment of the barrel mounting device of the cartridge type dental injection device according to the invention. This embodiment is basically identical to that illustrated in FIGS. 1, 2 and 3 and therefore, the like components are indicated by the like reference numerals. In the second embodiment of the invention, an annular cam surface 14 and a relieving surface 15 are provided on a locking ring 13 in a position reverse to that in the first embodiment of the invention. Hence, movement of the locking ring 13 to a position where the locking balls 8 are released from the annular groove 12 of the barrel 9, is in a direction reverse to that in the first embodiment, that is to say, in a direction away from the housing of the injection devise. A coil spring 16 is disposed between a shoulder of the annular cam surface 14 of the annular locking ring 13 and a retaining ring 5" fitted in a circumferential groove firmed on the outer periphery of the mounting member 5a to urge the locking ring 13 to the position where the annular cam surface 14 faces the locking balls 8, that is to say, in a direction away from the injection device. A stop ring 17 is fitted in a circumferential groove formed on the outer periphery of the mounting member 5a on the side of the relieving surface 15 of the locking ring 13 to serve to retain in place the locking ring 13 urged under action of the coil spring 16.

Figure 6:
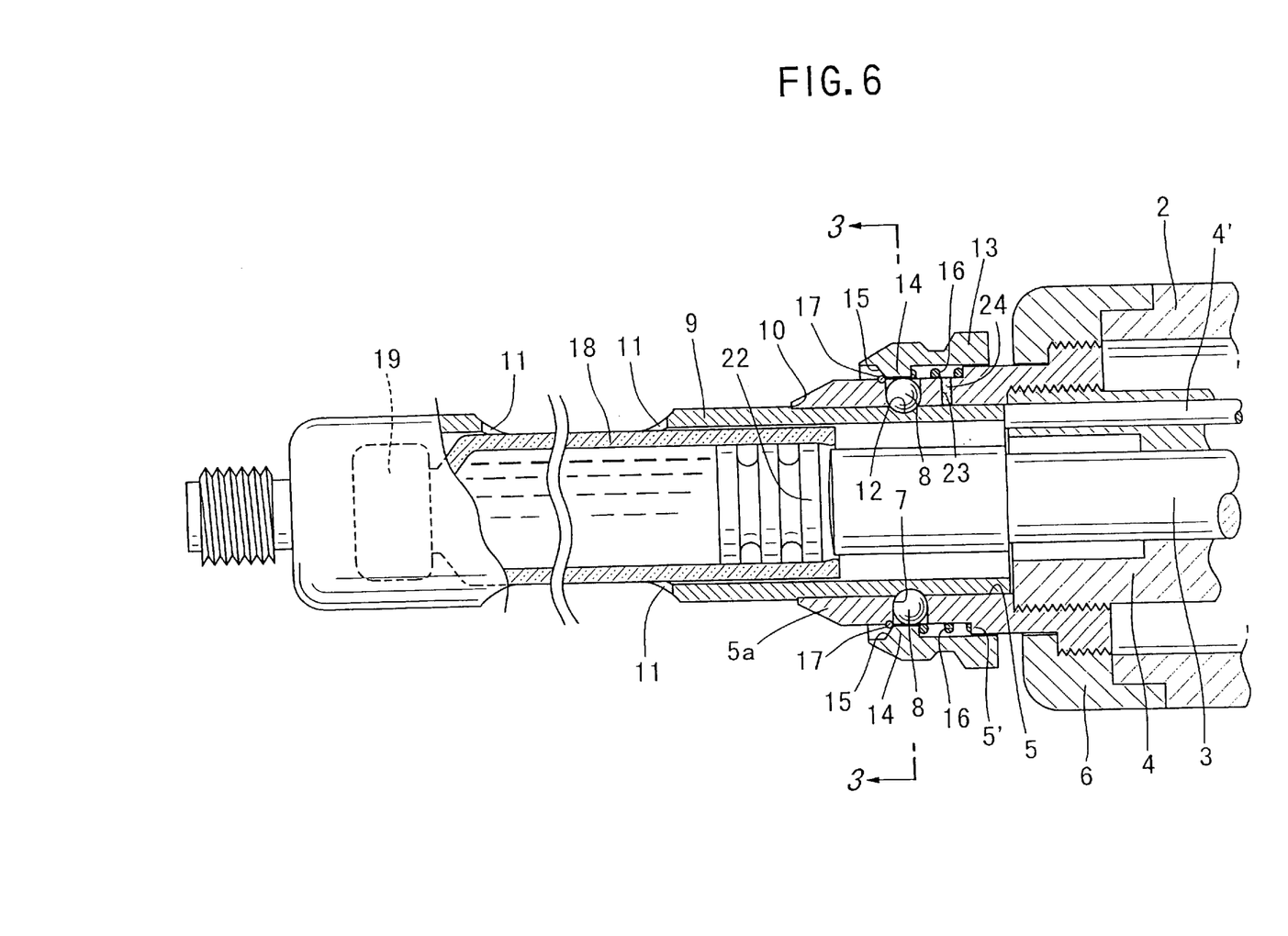
FIG. 6 is a view similar to FIG. 2, showing a cartridge type dental injection device according to a third embodiment of the present invention.

FIG. 6 illustrates the preferred embodiment of the invention similar to that of FIG. 2, with the exception of braking means for the barrel. The braking means comprises a piece of rubber 24 tightly fitted in an aperture 23 drilled radially in the mounting member 5a and preferably consisting of synthetic rubber, such as silicone rubber, nitrile rubber or the like. There may be provided more than one aperture and hence, more than one piece of rubber. In order to tightly fit the piece of rubber 24 in the aperture 23, the piece of rubber 24 preferably have a diameter slightly larger than that of the aperture 23. Prior to the tight fitting, a piece of rubber is cooled to a temperature below 10° C. to shrink it and then, the shrunk piece of rubber is inserted in the aperture. As the temperature of the piece of rubber returns to the ambient temperature, the piece of rubber expands to return to its original size for tight fitting of the piece of rubber in the aperture. Preferably, the piece of rubber is positioned in the aperture such that the inner end of the piece of rubber slightly protrudes radially inwardly beyond the inner surface of the socket in order to ensure a good contact of the piece of rubber with the barrel.

It will be appreciated that the braking means for the barrel may be applied to the embodiment of the invention illustrated in FIGS. 4 and 5.

Figure 7:
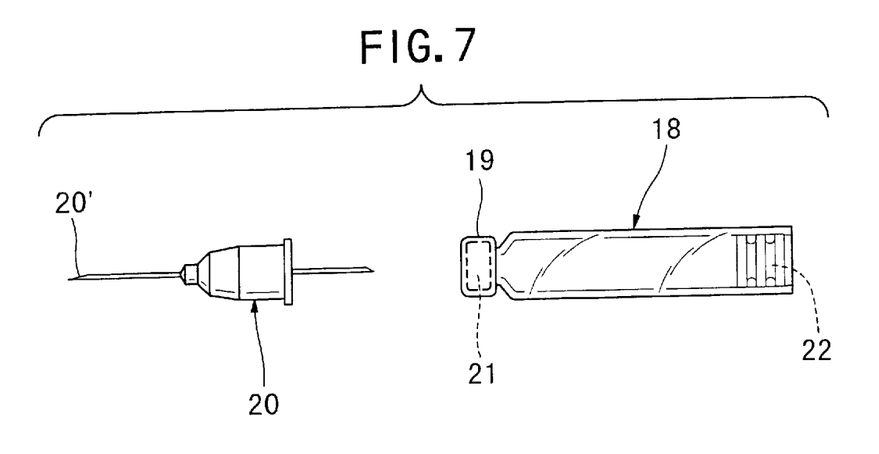
FIG. 7 is a schematic view of a cartridge and a needle to be utilized for the injection device of the invention.

Referring to FIG. 7, there is illustrated therein a well-known cartridge 18 to be used for the injection device of the invention, and the cartridge 18 comprises a rubber plug 21 retained at the end of the cartridge by a metallic cap 19 for sealing and adapted to be penetrated with a needle 20 of the needle fitting which is adapted to be threadedly secured to the barrel 9, and a plunger rubber 22 fitted in an open end of the cartridge and adapted to be pushed by the plunger rod 3 of the injection device for ejection of the injection liquid in the cartridge, through the needle. The needle has at its tip end a cut surface 20' to define a sharp cutting edge.

In use of the injection device of the invention, the locking ring 13 is manually pushed against action of the coil spring 16 to the position where the relieving surface 15 faces the locking balls 8 whereas the annular cam surface 14 of the locking ring 13 moves away from the locking balls. As a result, the locking balls 8 is free to move radially outwardly toward the relieving surface 15 so that the barrel 9 can be removed from or inserted in the socket 5. After from its rear open end, the barrel 9 removed from the socket 5 has been loaded with a cartridge 18, the barrel 9 is inserted in the socket 5 and then, the hand is released from the locking ring 13 so that it is returned to its original position under action of the coil spring. Thus, the annular cam surface 14 will engage the locking balls 8 to push radially inwardly them into the annular groove, thereby preventing the barrel from coming out of the socket. In this position, the barrel 9 is rotatable around it's axis so as to be capable of altering the orientations of the viewing window 11 in the barrel 9 and cut surface 20' of the needle 20 threadedly secured to the barrel 9 as desired. In the embodiment illustrated in FIG. 6, the barrel is in frictional engagement with the piece of rubber to prevent the barrel from unintentionally turning or rotating around it's axis, thereby, maintaining the desired orientations of the viewing window 11 and cut surface 20' of the needle 20 during injection.

When the needle 20 is threadedly secured to the forward end of the barrel 9, the inner needle portion pierces the rubber plug 21 of the cartridge 18 for communication with injection liquid in the cartridge. Thus, the injection liquid can be ejected through the needle by advancing the plunger rod 3 to push the plunger rubber 22. During this operation of injection, the most desired orientation of the viewing window in the barrel enables the dentist to visibly ascertain how much injection liquid in the cartridge has been injected therefrom.

What is claimed is:

1. A device for mounting cartridge receiving barrel in a cartridge type dental injection device comprising a mounting member having a socket defined thereby, a barrel adapted to be inserted in the socket and having diametrically opposite viewing windows formed therein, said mounting member having a plurality of circumferentially spaced apart ball retaining holes, and a locking ball placed in each of said holes, said barrel being provided with an annular groove adapted to receive a portion of each locking ball therein, and a locking ring having an annular cam surface and a relieving surface positioned adjacent to each other and movable between a position where when said locking balls are in alignment with said annular groove, said annular cam surface pushes said locking balls toward said annular groove to bring portions of said locking balls into engagement with said annular groove and a position where said relieving surface faces said locking balls to release them from said annular groove.

2. The device for mounting cartridge receiving barrel in a cartridge type dental injection device according to claim 1 wherein the movement of said locking ring from the position where said locking balls are released from said annular groove, may be in a direction toward said housing of said injection device.

3. The device for mounting cartridge receiving barrel in a cartridge type dental injection device according to claim 1 wherein the movement of said locking ring from the position where said locking balls are released from said annular groove, may be in a direction away from said housing of said injection device.

4. The device for mounting cartridge receiving barrel in a cartridge type dental injection device according to claim 1, further including a coil spring for urging said locking ring to the position where said annular cam surface faces said locking balls.

5. The device for mounting cartridge receiving barrel in a cartridge type dental injection device according to claim 1, further including means for determining the position to which said barrel can be inserted in said socket, said means comprising a shoulder of said barrel, adapted to abut the forward end of said barrel.

6. The device for mounting cartridge receiving barrel in a cartridge type dental injection device according to any one of claims 1~5 wherein said mounting member defining said socket may have a piece of rubber tightly fitted in an aperture drilled therein, said piece of rubber being in frictional engagement with a portion of the peripheral surface of said barrel to prevent it from unintentionally turning around it's axis relative to said socket.

* * * * *